(12) United States Patent
Dybbs

(10) Patent No.: US 6,228,099 B1
(45) Date of Patent: May 8, 2001

(54) OPHTHALMIC SURGICAL SYSTEM AND METHOD

(76) Inventor: Alexander Dybbs, 2588 Edgerton Rd., Cleveland, OH (US) 44118

( * ) Notice: Subject to any disclaimer, the term of this patent is extended or adjusted under 35 U.S.C. 154(b) by 0 days.

(21) Appl. No.: 09/197,021

(22) Filed: Nov. 20, 1998

Related U.S. Application Data

(60) Provisional application No. 60/066,725, filed on Nov. 21, 1997.

(51) Int. Cl.$^7$ ....................................................... A61F 9/00
(52) U.S. Cl. ........................................... 606/166; 606/167
(58) Field of Search .............................. 606/1, 167, 166, 606/169, 171, 172, 173, 176–178; 604/19, 22

(56) References Cited

U.S. PATENT DOCUMENTS

| Re. 35,421 | 1/1997 | Ruiz et al. . | |
|---|---|---|---|
| 4,173,980 | 11/1979 | Curtin . | |
| 4,660,556 | 4/1987 | Swinger et al. . | |
| 4,662,370 | 5/1987 | Hoffman et al. . | |
| 4,665,914 | 5/1987 | Tanne . | |
| 4,674,503 | 6/1987 | Peyman et al. . | |
| 4,688,570 | 8/1987 | Kramer et al. . | |
| 5,133,726 | 7/1992 | Ruiz et al. . | |
| 5,215,104 | 6/1993 | Steinert . | |
| 5,779,723 | * | 7/1998 | Schwind ................................ 606/166 |

FOREIGN PATENT DOCUMENTS

| 195 40 439 | 10/1995 | (DE) . |
| 0873735 | 10/1998 | (EP) . |
| 0895764 | 10/1999 | (EP) . |
| WO 95/28871 | 11/1995 | (WO) . |
| 9827901 | 2/1998 | (WO) . |

OTHER PUBLICATIONS

Kronemyer, Bob, "Advanced microkeratome simplifies ALK", Ocular Surgery News, Dec. 15, 1995.
"LaserSight launches new Ruiz microkeratome", Ocular Surgery News, Nov. 15, 1997.
Black, Harvey, "Newly developed microkeratome may ease LASIK", Ocular Surgery News, Jun. 1, 1996.
Nascimento, Ednei M.D. and Marcos Chaves Barbosa, M.D., "Keratome with clear corneal molder permits good cut for LASIK", Ocular Surgery News, Feb. 1, 1997.
Singer, Henry W., "Superior hinge LASIK with new microkeratome improves safety", Ocular Surgery News, Mar. 15, 1997.
Nordon, Lee T., M.D., "Avoiding LASIK complications takes patience", Ocular Surgery News, International Edition, Mar. 1997.
"Conventional Mechanical Microkeratomes", Ocular Surgery News, Aug. 1, 1998.
Bores, Leo D. M.D., *Refractive Eye Surgery*, Chapter 10 (1993) Published by Blackwell Scientific Publications, Inc.

* cited by examiner

*Primary Examiner*—Glenn K. Dawson
(74) *Attorney, Agent, or Firm*—Renner, Otto, Boisselle & Sklar, LLP

(57) ABSTRACT

A microkeratome for keratomileusis ophthalmic surgery having a base, a carriage mounted to the base and a cutting blade carried in the carriage. The carriage is guided for movement in an axial cutting direction and the cutting blade is movable in an oscillating motion transverse to the cutting direction. In addition, the carriage is movable in the cutting direction without imparting the oscillating motion to the cutting blade.

33 Claims, 9 Drawing Sheets

OPHTHALMIC SURGICAL SYSTEM AND METHOD

This application claims the benefit of U.S. Provisional Application No. 60/066,725, filed Nov. 21, 1997.

FIELD OF THE INVENTION

The invention relates to an ophthalmic surgical system and method including a disposable surgical microkeratome and, more particularly, to a surgical system and method for using such a device in laser in situ keratomileusis (LASIK).

BACKGROUND OF THE INVENTION

In the past thirty-five years, several opthalmic surgical methods and devices have been developed and increasingly are used to change the shape of the cornea to correct vision defects, including myopia, hyperopia and astigmatism.

An early technique included a "primary keratectomy" in which an anterior corneal lenticle is removed by manually pushing a blade of a microkeratome across the cornea. Then a "refractive keratectomy" is performed, wherein an optic correction is carved in the surface of the lenticle with a lathe similar to a contact lens lathe. The lenticle is sutured back in place on the eye. When an even and smooth cut is achieved, the best and most predictable results are obtained. However, the manual microkeratomes are difficult to use and require some skill to propel the blade across the cornea in an even and smooth manner, thereby providing varying qualities of primary keratectomies based on the skill and experience of the surgeon. As a result, the predictability of the refractive correction was minimal.

The methods and devices have evolved over the years to an automated, mechanical movement of the microkeratome blade across the cornea which provides a steady, even cut and which improves the predictability of the refractive correction. Furthermore, the lenticle is not completely severed from the cornea. Instead a flap is cut from the cornea, the back of the flap or the exposed stromal bed is sculpted in situ with a laser to provide the refractive correction, and the flap is replaced without sutures. This procedure is called laser in situ keratomileusis (LASIK). LASIK greatly improves the predictability of the amount of change in refractive correction and greatly reduces the amount of time required for the cornea to heal. In addition, the patient experiences a relative lack of discomfort from this procedure.

Unfortunately, problems still remain with some microkeratomes used to make the flap. Some existing microkeratomes still require the surgeon to estimate the length of the cut to make the flap because the cutting distance is not automated. Furthermore, generally microkeratomes are made of surgical steel which prevents the surgeon from viewing the cornea as the cutting blade oscillates and advances.

Another problem with some microkeratomes is that they are made of many small metal components which are expensive to produce and assemble. The assembled microkeratome may be less than two inches long, and individual components may be much smaller. As a result, cleaning and sterilization of the microkeratome between patients is very difficult. Sometimes the microkeratome must be at least partially disassembled and each component cleaned by hand. Therefore, the existing microkeratomes are difficult or even impossible to maintain in an acceptably sterile condition. Additionally, as one might imagine the assembly of many small parts while wearing sterile gloves is very difficult.

Some existing microkeratomes have one or more of the following problems in addition to those described above. For example, on some microkeratomes the depth of cut is determined by an adjustment plate which must be selected and added to the parts assembled before the operation. A last minute change may require the microkeratome to be disassembled, the adjustment plate changed, and then reassembled. Another problem is that some microkeratomes use a mechanical stop to halt the advance of the cutting blade, thereby stalling the motor. This damages the motor and reduces its useful life. Furthermore, some microkeratomes are relatively heavy, thus placing undue pressure on the eye and hindering precise location on the eye. Yet another problem with some microkeratomes is that a base must be attached to the eye and then a cutting device must be assembled and/or mounted thereon.

Therefore, a microkeratome which is easy to use, disposable or easy to clean, and performs a keratectomy in a consistent, smooth and reliable manner would be desirable.

SUMMARY OF THE INVENTION

The present invention provides a microkeratome and an associated opthalmic surgical system and method that overcome problems associated with the use of prior art microkeratomes. The present invention, inter alia, provides for independent control of the axial movement and transverse oscillation of a cutting blade of a microkeratome to provide a consistently high quality lamellar flap in the cornea of an eye. A preferred opthalmic surgical system includes a control assembly that powers and controls the movement of the cutting blade, which control assembly is preferably located remote from the microkeratome. This allows the microkeratome to be pre-assemblable, sterilizable, and preferably disposable. Furthermore, the microkeratome of the present invention preferably is made of a clear plastic, making the microkeratome lightweight and easy to produce and use, while allowing the surgeon to observe the cornea as the blade advances.

More particularly, one aspect of the invention provides a microkeratome for keratomileusis ophthalmic surgery having a base, a carriage mounted to the base and a cutting blade carried in the carriage. The carriage is guided for movement in an axial cutting direction and the cutting blade is movable in an oscillating motion transverse to the cutting direction. In addition, the carriage is movable in the cutting direction without imparting the oscillating motion to the cutting blade.

According to one embodiment of the invention, the movement of the carriage in the axial direction can be automated.

According to another embodiment of the invention, the carriage is connectable to an axial cable having a shaft movable within a sheath. In this embodiment the base of the microkeratome provides an axial retaining clip which engages an axial cable fitting on the cable to hold the sheath such that movement of the shaft imparts movement to the carriage relative to the base.

According to yet another embodiment of the invention, substantially all of the microkeratome is molded from a substantially transparent material.

Another aspect of the invention provides a system for keratomileusis ophthalmic surgery that provides a microkeratome for cutting a section of a cornea of an eye and a control assembly for controlling the microkeratome. The microkeratome provides a base, a carriage mounted to the base and a cutting blade carried in the carriage. The carriage is guided for movement in an axial direction. The control assembly includes an axial drive for generating linear movement and a rotary drive for generating rotational movement independently of the axial drive. The axial drive is connected to the microkeratome to impart axial movement to the carriage in an axial direction relative to the base and the rotary drive is connected to the microkeratome to impart an oscillating movement to the cutting blade transverse to the axial direction. The control assembly also includes a controller which controls the axial drive and the rotary drive.

According to one embodiment of the invention, the axial shaft is connected to the carriage with a coupling that permits the axial cable to rotate without imparting torque to the carriage.

According to another embodiment of the invention, the control assembly includes a suction device for supplying suction pressure to the microkeratome. The suction device is connected to the microkeratome for generating a partial vacuum in a suction chamber mounted to the base to maintain a position of the base relative to an eye.

According to another embodiment of the invention, the controller stops operation of the axial drive and the rotary drive if the suction pressure drops below a predetermined value.

Yet another aspect of the invention provides a method for keratomileusis opthalmic surgery that includes linearly advancing a cutting blade of a microkeratome from an initial position in an axial direction while simultaneously oscillating the cutting blade in a direction transverse to the axial direction; stopping the linear advance and transverse oscillation of the cutting blade at an end position which is removed from the initial position; and linearly retracting the cutting blade to the initial position without imparting transverse oscillation to the blade.

According to one embodiment of the invention, stopping the linear advance and transverse oscillation of the cutting blade occurs automatically at a predetermined distance from the initial position.

According to another embodiment of the invention, the method includes selecting one of a plurality of microkeratomes which provide for respective depths of cut.

According to another embodiment of the invention, the method includes disposing of a first microkeratome following a first operation and selecting a second microkeratome for a subsequent operation.

According to yet another embodiment of the invention, the method includes automatically stopping the cutting blade when the suction device fails to maintain a predetermined level of suction pressure.

Another aspect of the invention provides a method for keratomileusis opthalmic surgery that includes connecting a disposable microkeratome to a control unit operative to drive and control a cutting action of the microkeratome; using the microkeratome to at least partially remove a section of a patient's cornea; and discarding the microkeratome after use with a single patient.

Yet another aspect of the invention provides a microkeratome having a base, a carriage mounted to the base for movement, and a cutting blade carried by the carriage for movement therewith, and the base and carriage are formed of a molded transparent plastic material.

The foregoing and other features of the invention are hereinafter fully described and particularly pointed out in the claims, the following description and annexed drawings setting forth in detail a certain illustrative embodiment of the invention, this embodiment being indicative, however, of but one of the various ways in which the principles of the invention may be employed.

DETAILED DESCRIPTION

The present invention provides a system and method using a disposable microkeratome that facilitates the performance of corrective refractive opthalmic surgery, particularly keratomileusis, and more particularly laser in situ keratomileusis, LASIK, with independent control of a transverse oscillating motion, an advancing motion, and a retracting motion of a cutting blade.

Figure 1:
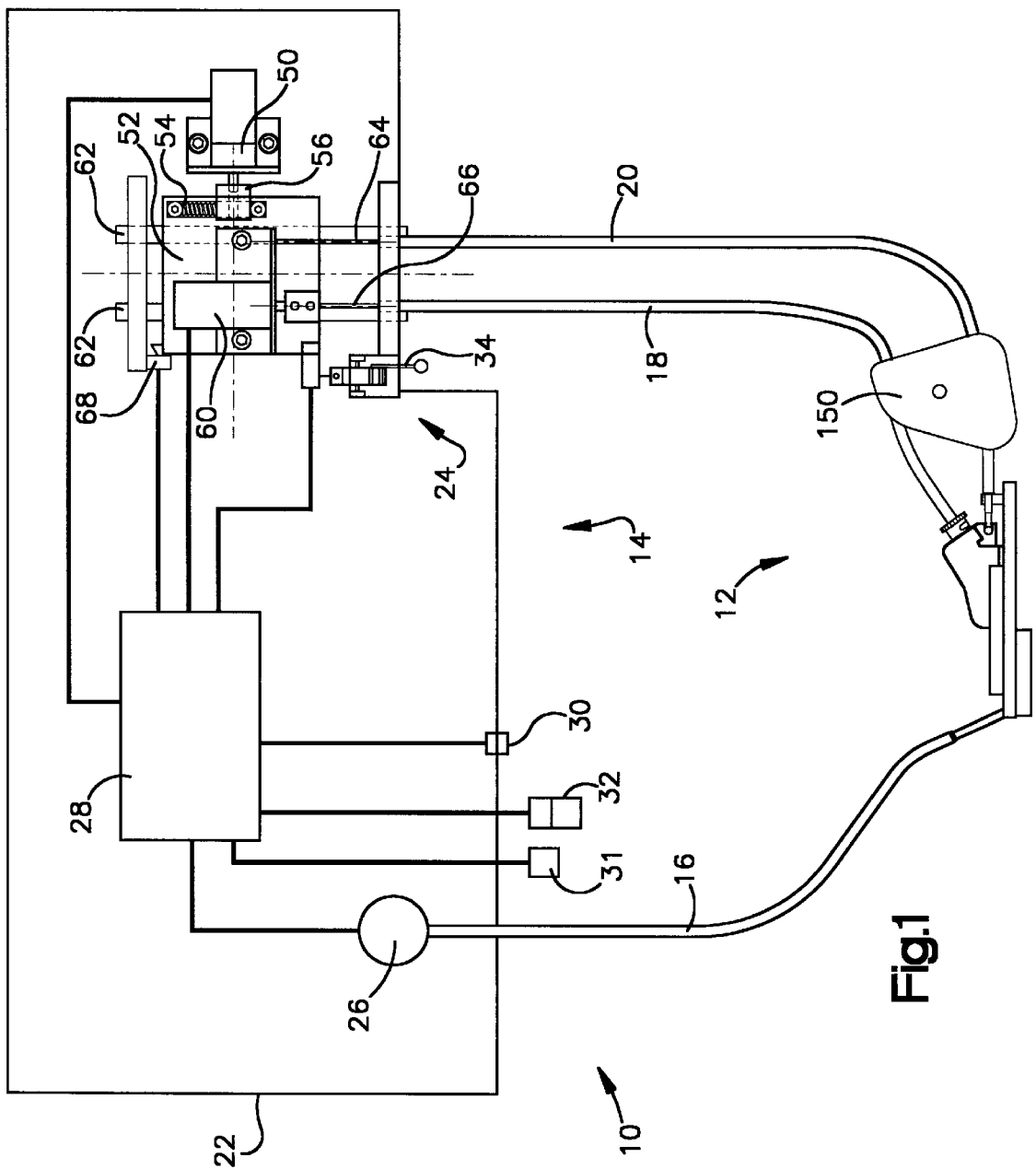
FIG. 1 is a schematic view of the opthalmic surgical system according to the present invention.

Referring now to the drawings in detail and initially to FIG. 1, a preferred embodiment of the ophthalmic surgical system 10 includes a disposable surgical microkeratome 12 according to the present invention. In addition to the disposable microkeratome 12, the system 10 includes a control assembly 14, a flexible suction line or tube 16, and a pair of flexible control cables 18 and 20. The suction line 16 and flexible control cables 18 and 20 are connected between the control assembly 14 and the microkeratome 12 for remotely controlling and driving the microkeratome 12. The control assembly 14 includes control and driving components that are more expensive to produce and are intended to be reused for surgery on many patients, whereas the microkeratome is made of relatively inexpensive components and is intended to be used once then discarded. The control assembly 14 is removed from the surgical area and thus away from the patient, thereby preventing contamination of the control assembly by the patient, and vice versa.

In contrast, the microkeratome 12, which comes into direct contact with the patient, may be used on a single eye or a pair of eyes on a single patient and then discarded. The microkeratome 12 preferably is formed primarily of a few molded plastic parts that are easy to assemble, whereby the microkeratome is inexpensive to produce. The microkeratome can be provided completely assembled, sterilized and ready for use. Since only the microkeratome 12 comes into contact with the eye, does not require extensive assembly just prior to surgery and is disposable, the system 10 is more easily and more effectively maintained in a clean and sterile condition.

The control assembly 14 is contained within a housing 22 and includes a drive assembly 24, a suction pump 26, and a controller 28. The controller 28 preferably includes an electronic circuit for controlling the operation of the drive assembly 24 and the pump 26. The control assembly 14 also has several input devices connected to the controller, including an ON/OFF switch 30, a one-position suction pedal or switch 31, a two-position foot pedal or switch 32, and a flap length adjustment selector 34, also called a flap hinge positioning system. The input devices permit the surgeon to control several variables in the operation of the system 10, as further described below.

Figure 2:
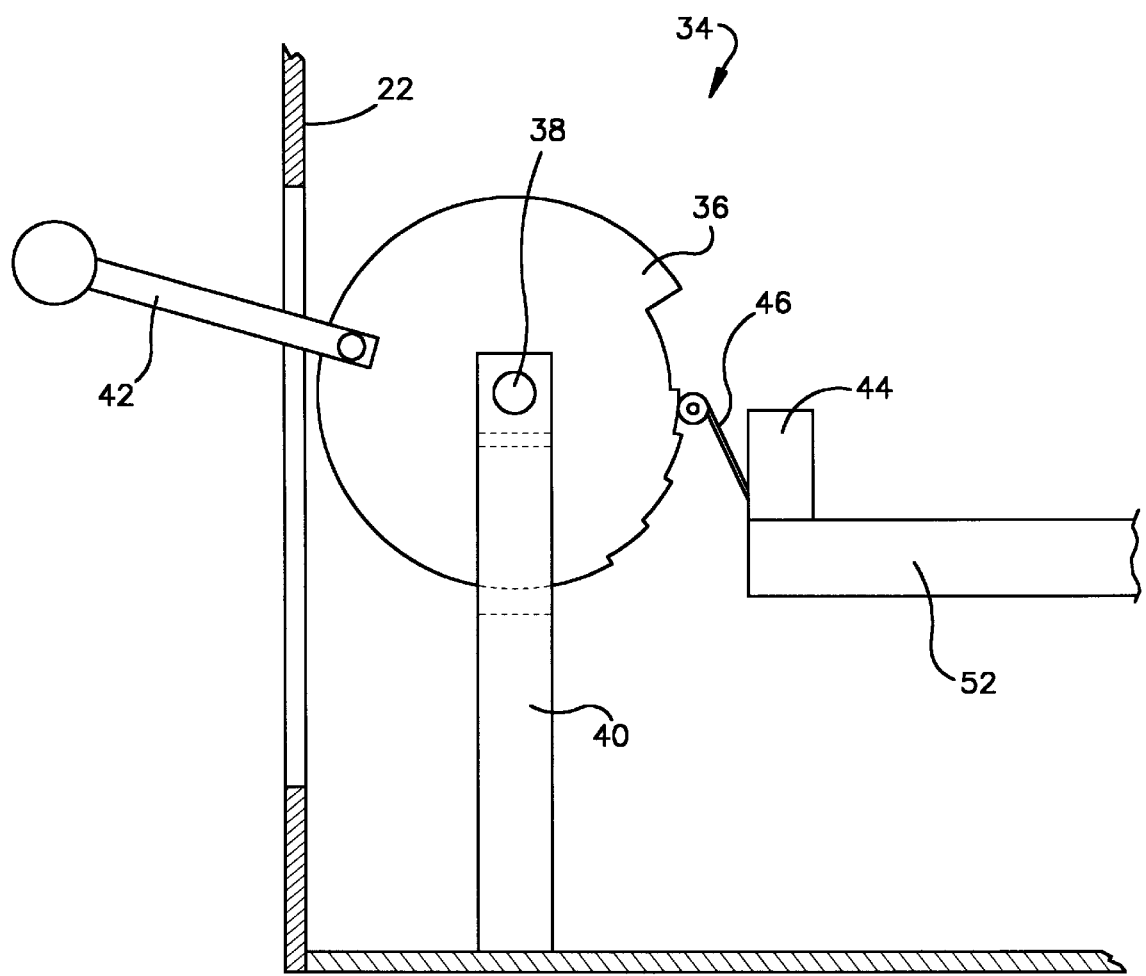
FIG. 2 is a side view of a flap length adjustment selector according to the present invention shown in a cutaway view of the control assembly housing.

Because each eye is a different size and has a different curvature, the position of a flap hinge or the length of a flap (or the width of a severed section) is desirably selected by the flap length adjustment selector 34 prior to operation of the system 10. As shown in FIG. 2, the flap length adjustment selector 34 includes a stepped cam device 36 mounted generally in the form of a disk with a stepped cam edge surface. The cam 36 is mounted for rotation by a pivot axle 38 supported between a pair of laterally spread apart support arms 40 (one shown). A control arm 42 is connected to the cam 36 and extends through the housing 22 for rotating the cam to various positions. The flap length adjustment selector 34 also includes a flap length microswitch 44 mounted to a slide member 52 (FIG. 1) discussed in greater detail below. The flap length microswitch 44 includes a microswitch arm 46 which extends toward the cam 36.

The microswitch 44 provides a signal to the controller 28 (FIG. 1) indicating that the desired cutting length has been reached. Although the stepped cam 36 is part of the illustrated embodiment for selecting the desired cutting length, other types of input devices may be used, including but not limited to a dial indicator, a pushbutton selector, an electronic keypad, or microcomputer input devices such as a keyboard, a liquid crystal display and/or a mouse.

Generally, the control assembly 14 (FIG. 1) controls the microkeratome 12 for severing the cornea, thus leaving a flap that remains attached to the cornea by a hinge. The flap preferably has a uniform thickness and a length of about three-quarters of the distance across the cornea, about nine to twelve millimeters. Alternatively, the control assembly could direct the microkeratome to completely server the section from the cornea.

Returning to FIG. 1, the drive assembly 24 includes a linear drive motor 50 connected to a slide member 52, for example by rack 54 and pinion 56, respectively, for moving the slide member 52 through a range of linear motion corresponding to the desired cut length. An initial position microswitch 68 is located at one end of the range of motion for the slide member 52. The flap length microswitch 44 is mounted to the slide member 52 and contacts the cam 36 (FIG. 2) of the flap length adjustment selector 34 at the opposing end of the range of motion for the slide member. The microswitches 68 and 44 are connected to the controller 28.

The slide member 52 is mounted on a pair of parallel rods 62 which act as slide guides for directing or guiding the motion of the slide member 52 in a linear direction. A rotary drive motor 60 is carried on the slide member 52 for movement therewith. The axial cable 20 includes an axial drive shaft 64 that is connected to the slide member 52 for translating the linear motion of the slide member 52 to the microkeratome 12 and the rotary cable 18 includes a rotary drive shaft 66 that is connected to the rotary motor 60 for transferring rotational motion to the microkeratome 12. Because the rotary drive motor 60 is mounted on the slide member 52, the rotary drive shaft 66 also simultaneously moves in a linear direction with the slide member 52. Therefore, both the axial drive shaft 64 and the rotary drive shaft 66 linearly advance and retract with the slide member 52.

The rotary drive shaft 66 preferably has a monocoil, double wound or triple wound construction over a central wire or mandrel with the winds pitched in opposite directions to provide torsional rigidity. The rotary drive shaft is preferably made of stainless steel wire due to the strength and endurance limit of stainless steel and, more preferably, the shaft is made of 302 stainless steel. The triple wound construction provides better bi-directional properties as well as greater flexibility which increase the endurance life of the shaft, compared to a monocoil or double wound construction. The torsional stiffness of the triple wound construction is equivalent to or greater than the double wound construction but its flexural stiffness is less than half that of the double wound construction. This is particularly desirable since the shaft may rotate in a relatively sharp bend, at high speed. Furthermore, the rotary drive shaft 66 is coated with a very thin wall shrink tubing in order to provide a smooth surface to minimize or eliminate vibration. Thus, the rotary drive shaft is designed to rotate at speeds up to twenty thousand revolutions per minute and to provide the necessary torque to the microkeratome 12.

In contrast, the axial drive shaft 64 is preferably double wound over a central wire or mandrel. The winds are pitched in opposite directions to provide some torsional rigidity. The pitch angles, or helix angles, are preferably less than forty degrees to make the shaft more flexible than a traditional push-pull cable. However, the central mandrel or wire is larger in diameter than the wires in the outer layers to increase axial and flexural rigidity. This combination provides optimum flexibility without sacrificing "pushability" or the ability to transmit an axial force from the axial motor 50 to the microkeratome 12.

Both the axial and rotary drive shafts 64 and 66 are disposed in flexible sheathes 68 and 70 respectively. The rotary and axial drive shafts 66 and 64 and sheathes form the rotary drive cable 18 and the axial drive cable 20, respectively. The rotary drive cable 18 and the axial drive cable 20 connect the rotary drive motor 60 and the axial drive motor 50, respectively, to the microkeratome 12. The axial drive shaft 64 moves through the cable 20, as the slide member 52 moves through its range of motion while the rotary drive shaft rotates and moves axially within the sheath 70. Preferably, the inside of the sheathes are coated with a material, such as polytetrafluoroethylene (PTFE), to reduce friction between the sheathes and the cables.

Figure 3:
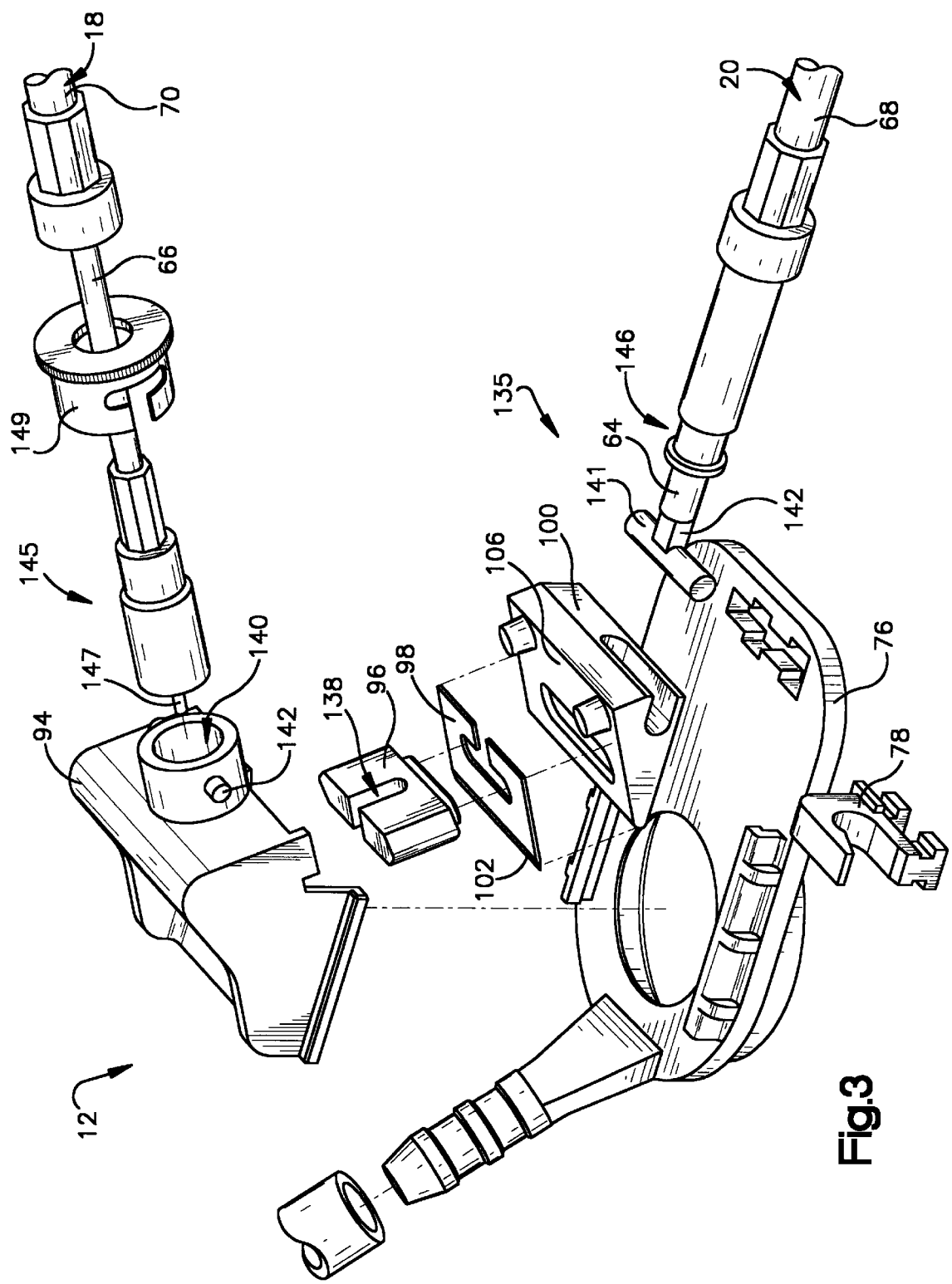
FIG. 3 is an exploded perspective view of the microkeratome according to the present invention looking down toward the top and one side of the suction platform.
Figure 4:
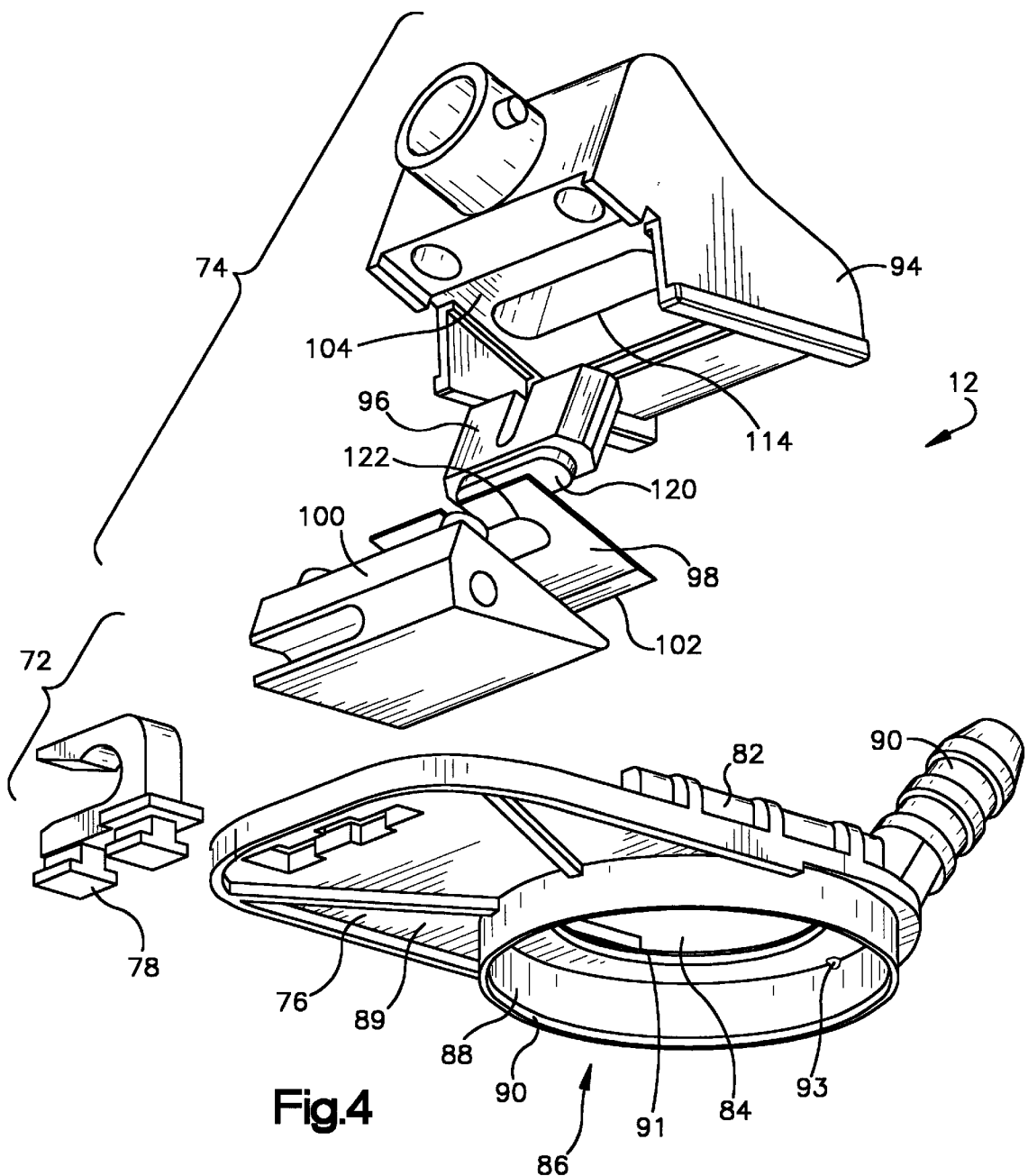
FIG. 4 is an exploded perspective view of the microkeratome according to the present invention as seen from below the suction platform.

FIGS. 3 and 4 show exploded perspective views of the microkeratome 12 and its components. The microkeratome 12 includes two main structures, i.e., a base 72 and a cutting assembly 74. The base 72 provides for locating the microkeratome on an eye and the cutting assembly 74 is movably mounted to the base for cutting the flap from the cornea.

Figure 5:
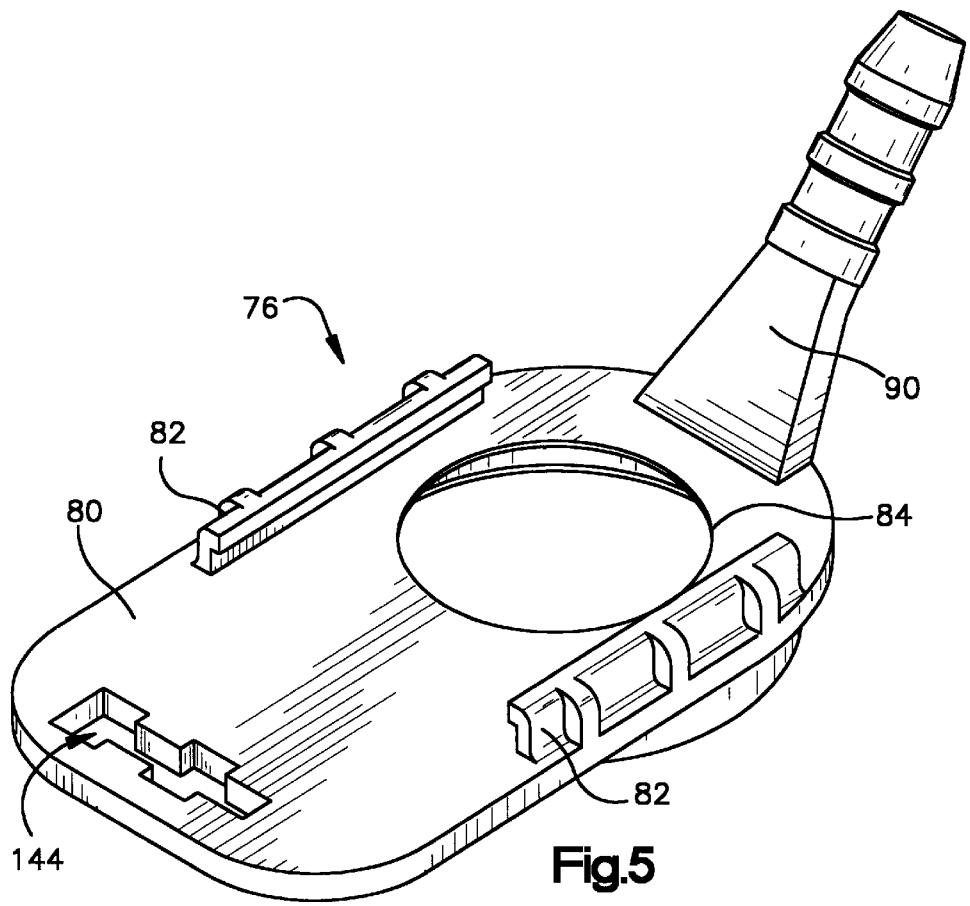
FIG. 5 is a perspective view of the suction platform.

The base 72 includes a suction or support platform 76 and a substantially C-shape anchor or retaining clip 78. The platform 76, shown in FIGS. 4 and 5, has a substantially flat and substantially rectangular top surface 80 on which the cutting assembly 74 slides. At the longer sides of the rectangular top surface 80, the platform 76 includes a pair of parallel guides 82. The illustrated preferred guides are generally L-shape and oppose each other cooperatively to form a track or guideway which restrains and guides the cutting assembly 74 for movement in an axial direction along the platform 76. The track functions to restrain and guide the cutting assembly 74, or more particularly a carriage portion 75 thereof, such that the cutting assembly 74 can only move forward and backward in an axial direction parallel to the length of the platform guides 82. The track also functions to hold the carriage to the platform 76 against any significant separation, thereby maintaining a smooth bottom surface of the carriage in stable sliding engagement with the top surface 80 of the platform. Of course, other suitable means may be devised for linearly guiding the carriage relative to the support platform.

At a front end of the platform 76 between the platform guides 82, a circular opening 84 is provided for receiving a cornea therethough. The circular opening 84 provides a sufficiently large aperture size for cutting a desired size flap in hyperopia. The opening 84 communicates through the top surface 80 (or actually top wall) of the platform 76 to a substantially cylindrical suction chamber 86 provided at the underside of the platform.

The suction chamber 86 is formed in part by a cylindrical suction ring 88 which depends from the top wall 89 of the platform 76 and is larger than the circular opening 84 in the platform 76. The suction ring 88 has a lower circular sealing edge for engaging and sealing against the surface of an eye. The circular opening 84 also is bounded by a sealing edge 91 for sealing against the eye. The sealing edges preferably are beveled to provide an airtight enclosed space or are otherwise configured to form a tight seal with the eye. In addition, the suction chamber 86 may include at its bottom surface thereof a material (coating or sealant) which improves the contact with the eye so that a partial vacuum can be drawn in the suction chamber to hold the platform to the eye. A silicone sealant may be used, for example.

The platform 76 has extending upwardly from a forward end thereof a fixture (or fitting) 90 which preferably performs multiple functions. The fitting provides for attachment of the suction line 16 (FIG. 11) to the platform, the angled fitting having a passage 93 (FIG. 4) extending to the suction chamber 86. Preferably the fixture 90 is angled away from the cutting assembly 74 to provide an unobstructed view of the cornea through the opening 84. The suction line 16 is connected to the suction pump 26 (FIG. 1) or other suitable vacuum source to provide suction to the suction chamber 86.

Suction is applied to the suction chamber 86 to create a partial vacuum which retains the platform 76 in a stable and fixed position relative to the eye. Preferably, the suction pump 26 (FIG. 1) creates suction in such a way that when the platform 76 adheres to the cornea, the intraocular pressure in the eye is raised to and maintained at at least about sixty millimeters of mercury. The platform 72 also is designed such that when suction is applied to the suction chamber 86, the cornea protrudes through the circular opening 84 and above the top surface 80 of the platform.

The fixture 90 also functions as a handle for manipulating the microkeratome. The surgeon can use the handle to facilitate positioning of the microkeratome on an eye and hold the microkeratome in place until a partial vacuum is drawn in the suction chamber. In fact, the surgeon can alternately use the handle to hold the microkeratome in place during the surgical procedure without using the vacuum hold-down, although this is less desirable.

As mentioned above, the platform 76 has at a back end thereof a retaining clip 78. The retaining clip 78 may be formed integrally with the platform or may be fixed thereto by suitable means, such as one or more anchor drivers inserted, as by snapping, into one or more slots or holes in the platform. Any suitable method of attachment may be used, such as the illustrated T-shape rails 152 or arrow shape clips which snap into position when pressed into corresponding openings in the platform.

Figure 10:
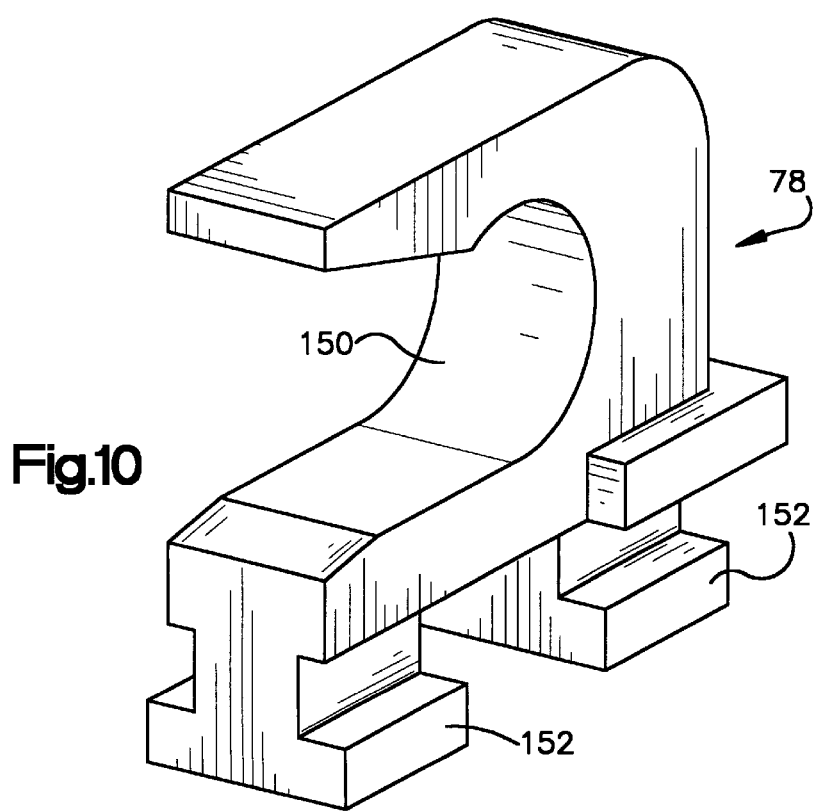
FIG. 10 is a perspective view of the axial retaining clip.

Referring briefly to FIG. 10, the retaining clip 78 has a C-shape body portion 150 that anchors the outer sheath 68 of the axial driver cable 20 relative to the platform 72 by engaging a groove in a sheath fitting 146 at the end of the axial cable 20. The axial shaft 64 (FIG. 1) is connected to the carriage 75 (as more particularly described below) and moves with the cutting assembly 74 (FIG. 3) axially forward and backward relative to the platform. The retaining clip 78 also functions, along with the fixture 90, to retain the cutting assembly 74 between the platform guides 82 and prevent the cutting assembly from disengaging the platform guides 82.

Figure 6:
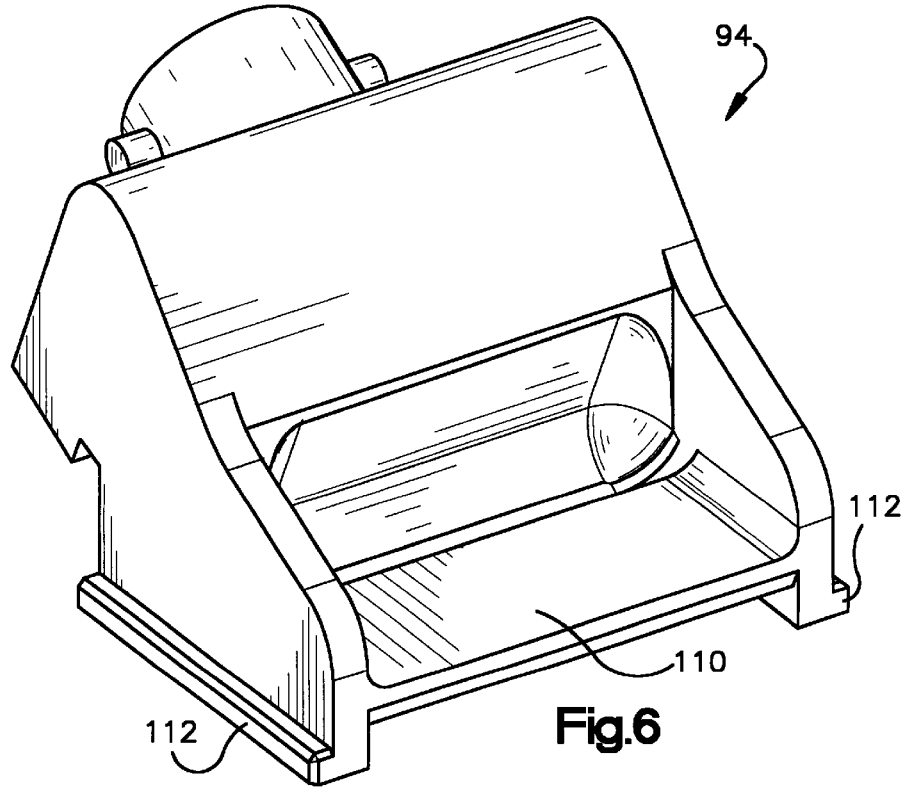
FIG. 6 is a perspective view of the top of the cutting head.
Figure 7:
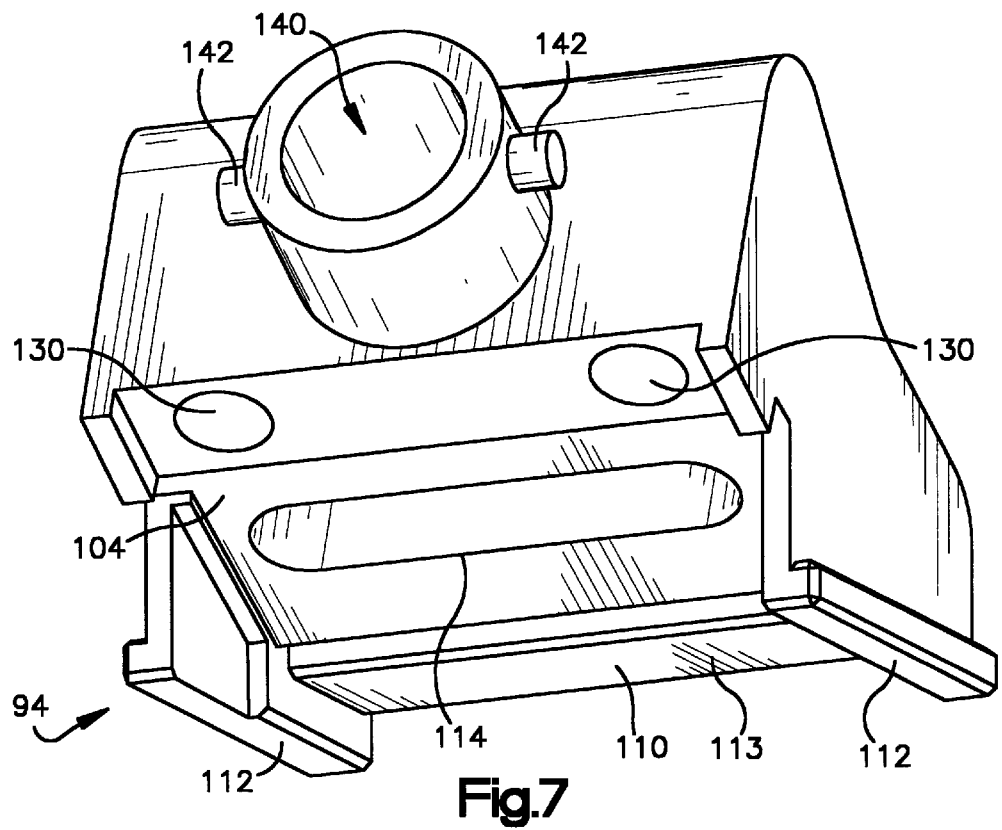
FIG. 7 is a bottom perspective view of the cutting head.

Returning to the cutting assembly 74, as illustrated in FIGS. 3 and 4 the cutting assembly includes a cutting head 94, a blade holder 96, a cutting blade 98, and a wedge 100. The cutting head 94 is shown in top and bottom perspective views in FIGS. 6 and 7, respectively. The cutting head includes a forward sled 110 at a forward end of the cutting assembly 74 (FIG. 3). The sled 110 forms a shelf which is interposed between a pair of rails 112 extending from the sides of the cutting head 94. The rails 112 are parallel to and slidingly engage the platform guides 82 (FIG. 5) on the platform 76 (see FIG. 5). As the cutting assembly 74 (FIG. 3) moves across the circular opening 84 (FIG. 4), a bottom surface 113 of the sled 110 engages and flattens the surface of the eye in preparation for cutting the flap by the trailing cutting blade 98. (See FIG. 14)

Behind the sled 110 the cutting head 94 also includes an angled blade guide surface 104 on the underside of the cutting head 94. The blade guide surface 104 is angled relative to the top surface 80 of the platform 76 to provide a desired cutting angle for the cutting blade.

The cutting head 94 has formed therein a transverse slot 114 that opens to the angled blade guide surface. The slot 114 slidably receives and guides the blade holder 96 (FIG. 3) for transverse reciprocating movement. The width of the slot is transverse to the direction of motion of the cutting head 94. The transverse slot 114 is wider in a transverse direction than the blade holder 96 (FIG. 3) to permit the blade holder 96 (FIG. 3) to oscillate within the slot 114. The transverse oscillation of the blade holder 96 creates a transverse oscillation of the cutting blade 98 which is anchored to the blade holder as discussed below.

The cutting blade 98, shown in FIGS. 3 and 4, has a cutting edge 102 which preferably is held at an angle transverse to the direction of motion of the cutting assembly 74, and more preferably at an angle of at least twenty-six degrees relative to the forward axial direction. The cutting blade 98 is held at an angle to the surface 80 of the platform 76 between the angled blade guide surface 104 of the cutting head 94 and a parallel angled top surface 106 of the wedge 100. The cutting edge 102 and the cutting blade 98 may be held at other angles, however, relative to the top guide surface 80 and/or the direction of motion.

Figure 14:
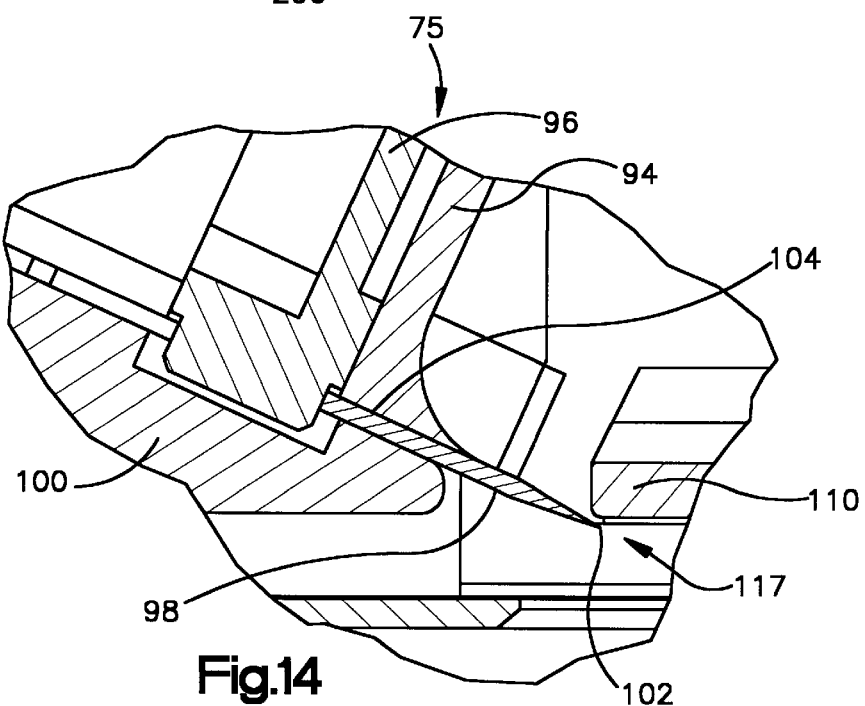
FIG. 14 is a partial cutaway view of the microkeratome of the present invention.

As last seen in FIG. 14, the cutting edge 102 of the cutting blade 98 extends beyond the angled surface 104 into the space between the cutting head 94 and the surface 80 of the platform 76. The distance between the cutting edge 102 (FIG. 3) and a bottom surface of the sled 110 forms a blade gap distance 117. The blade gap distance determines the thickness of the flap, preferably about one hundred fifty to one hundred sixty micrometers.

Figure 8:
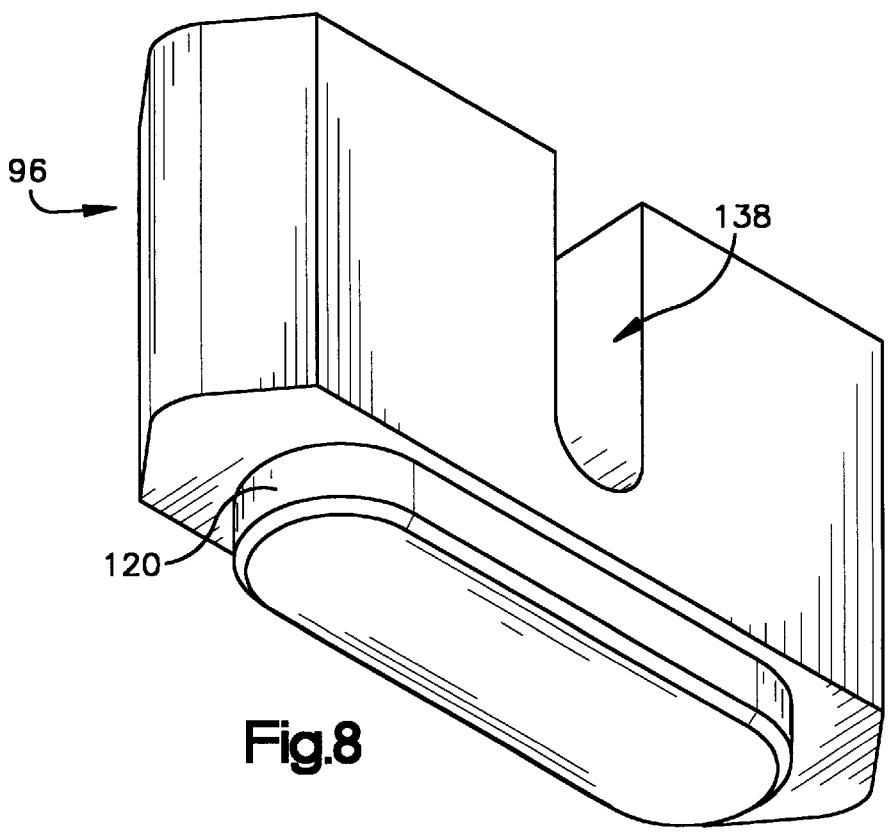
FIG. 8 is a perspective view of the blade holder.

FIGS. 4 and 8 illustrate the blade holder 96 which has a protrusion 120 that closely fits through an opening 122 in the cutting blade 98. The sides of the protrusion 120 of the blade holder 96 engage the sides of the opening 122 in the cutting blade 98 which is thereby held for movement with the blade holder 96. In the preferred embodiment, the blade holder 96 and the cutting blade 98 oscillate in a transverse direction which is perpendicular to the forward axial direction.

The blade holder 96 also includes a vertical slot 138 which is perpendicular to the width of the blade holder and perpendicular to the angled blade surface 104. When the blade holder is assembled in the cutting head 94, the slot 138 is aligned with an angled opening or passage 140 in the cutting head 94. The passage 140 also is perpendicular to the transverse slot 114 and parallel to the blade guide surface 104.

Figure 9:
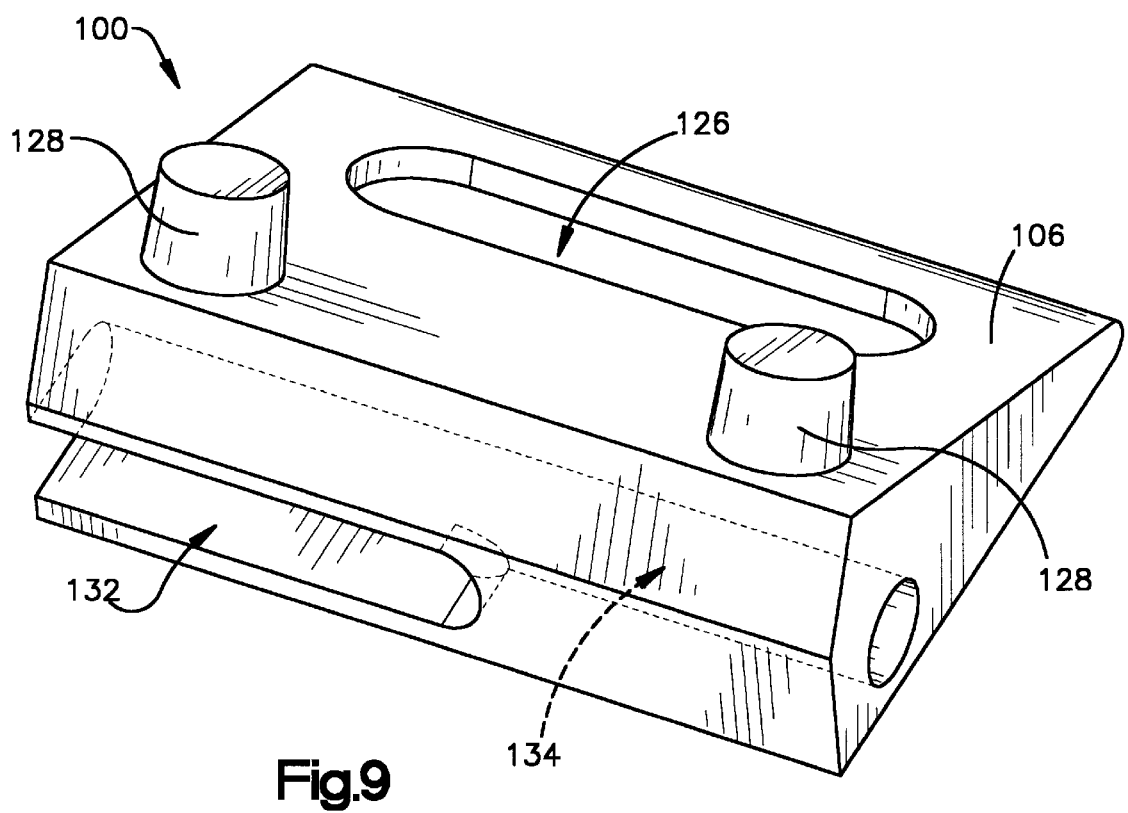
FIG. 9 is a perspective view of the wedge.

FIGS. 3 and 9 show the wedge-shape wedge 100 which holds the cutting blade 98 and the blade holder 96 in the cutting assembly 74. The wedge 100 has an approximately triangular cross-section with a thinner portion facing toward the cutting edge 102 of the cutting blade 98. The angled top surface 106 supports the cutting blade 98 as it oscillates with the blade holder 96. The cutting head 94 and/or the wedge 100 form the carriage 75 which carries and supports the cutting blade 98.

The wedge 100 also has a transverse recess 126 in the angled surface 106 which receives a distended portion of the protrusion 120 (FIG. 8) in the blade holder 96 (FIG. 8) that extends beyond the cutting blade 98. The transverse recess 126 extends parallel to and substantially coextensive with the transverse slot 114 (FIG. 7) in the cutting head 94 (FIG. 4) which receives the blade holder 96 (FIG. 8).

The wedge 100 also includes a pair of protrusions 128 extending substantially perpendicular from the angled top surface 106. These protrusions 128 are adapted to be press fit or otherwise secured in a pair of corresponding recesses 130 (FIG. 9) in the underside of the cutting head 94. The recesses 130 cooperate with the protrusions 128 to locate and hold the wedge 100 in place relative to the cutting head. The wedge 100 locks the cutting blade 98 and the blade holder 96 in the cutting head 94 while allowing the cutting blade 98 and the blade holder 96 to oscillate. Although the nature of the fit should hold the wedge 100 in place, preferably a surgical adhesive or medical grade epoxy is used with the protrusions and recesses to ensure that the wedge 100 remains in place. Additional respective recesses and protrusions in the form of locating pins and holes may be used to positively locate the position of the wedge relative to the cutting head.

The thicker side, or the back end of the wedge 100, has a groove 132 extending approximately halfway across the width of the wedge 100 and a bore 134 extending from the deepest portion of the groove 132 and coaxial therewith through the remaining width of the wedge 100. The groove 132 and bore 134 are adapted to receive a T shape pin 135 (FIG. 3) extending from an end of the axial shaft 64 (FIG. 1). The pin 135 and slotted bore 134 provide for quick connection of the axial shaft 64 to the wedge, although other suitable, preferably quick connect, means may be employed as desired.

Referring to FIG. 4, in summary the cutting assembly 74 includes the cutting head 94, the blade holder 96 which is received in the transverse slot 114 of the cutting head, and the cutting blade 98 which receives the protrusion 120 on the blade holder within an opening 122. The blade holder and the cutting blade are held in the cutting assembly by the wedge 100 and the cutting assembly is mounted on the platform assembly 72 between the platform guides 82. Preferably, each part of the microkeratome 12 (aside from the cutting blade) is composed of transparent materials, and preferably are molded plastic pieces, to permit the surgeon to better see what is happening during the operation.

Figure 11:
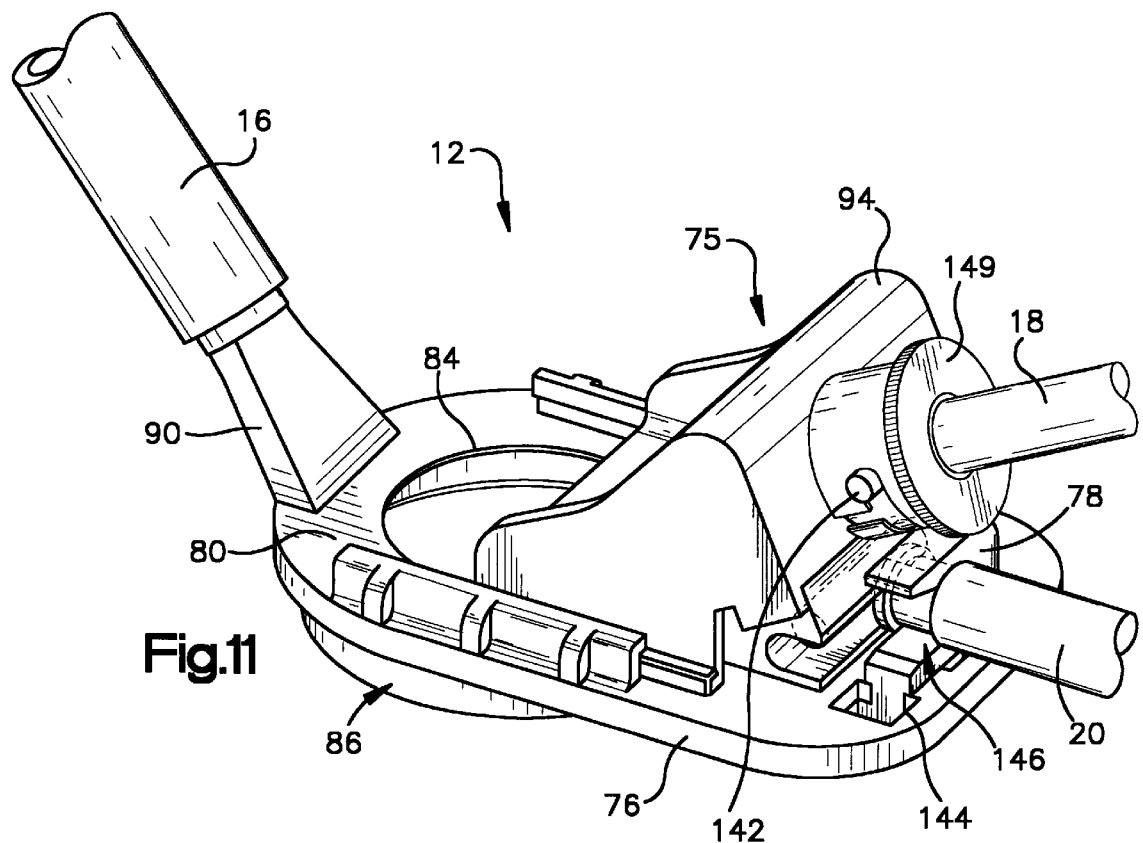
FIG. 11 is a perspective view of the microkeratome in a first position showing the connections of the control cables and the suction tube.
Figure 12:
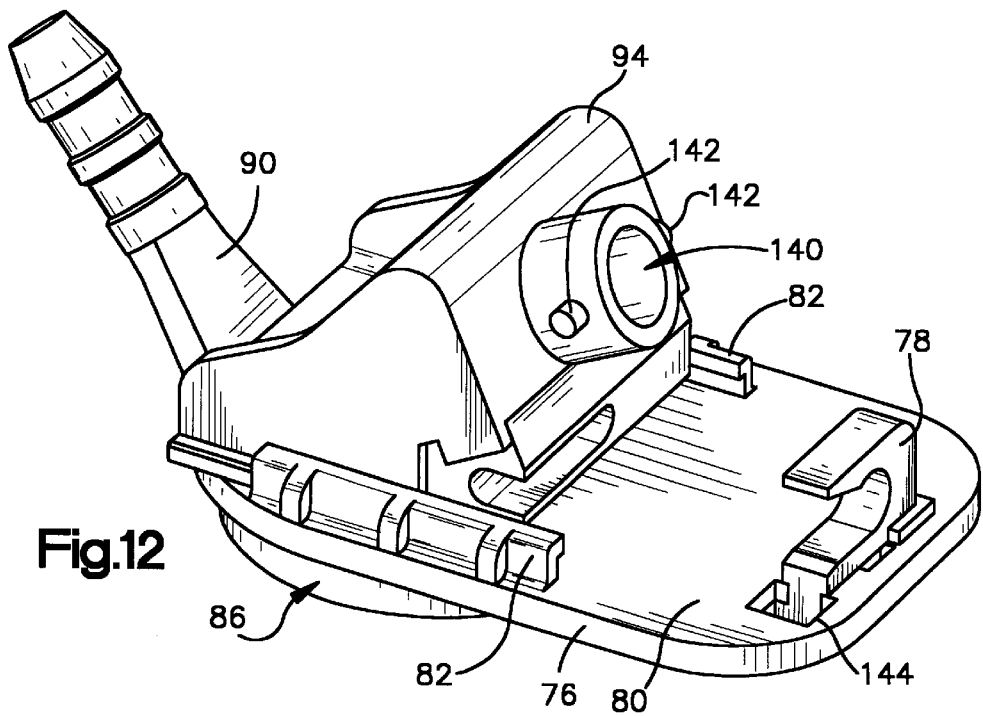
FIG. 12 is a perspective view of the microkeratome in a second position.

Turning to FIGS. 3 and 11, when assembled in the system 10 (FIG. 1), the microkeratome 12 is connected to the control assembly 114 through the cables 18 and 20. The axial drive shaft 64 is connected to the wedge 100 with the above described T pin and slot arrangement and the rotary drive shaft 66 is connected to the blade holder 96 through an eccentric 147 and a bayonet connection 149. The T shape pin 135 has a top crossing member 141 which is rotatably coupled to a trunk member 143 which is axially aligned with and fixed to the axial shaft 64. The rotatable connection permits the axial drive shaft 64 and the trunk member to twist without transmitting a torque to the cutting assembly 74. Other types of connecting devices for connecting the axial drive shaft to the cutting assembly may be used, including but not limited to screws, bolts, rivets, adhesives, etc., however, the axial drive shaft 64 preferably is free to rotate relative to the connecting device. Furthermore, the axial drive shaft may be connected to another part of the cutting assembly other than the wedge. For example, the axial shaft may be connected to the cutting head 94.

A fitting 146 on the axial drive cable 20 engages the retaining clip 78 to anchor the cable sheath 68 to the section platform 76 so that movement of the axial drive shaft 64 relative to the platform directly and precisely corresponds to movement of the sliding member 52 (FIG. 1). It is noted that the end of the sheath 68 is anchored to the housing 22. The axial drive shaft 20 (FIG. 1) pushes the carriage 75 during cutting and pulls the carriage back during a retractive stroke across the top surface 80 (FIG. 5) of the platform 76.

In contrast, the rotary shaft 66 has a fitting 145 with the eccentric 147 coupled to the rotary shaft 66 (FIG. 1). The eccentric passes through the passage 140 in the cutting head 94 to engage the vertical slot 138 in the blade holder 96. The eccentric is held engaged with the cutting head 94 by a bayonet coupling 149 which engages a pair of opposing pins 151 on a tubular coupling on the cutting head 94. The bayonet coupling is held in place with friction and permits the rotary shaft 66 to rotate in either direction while retaining the fitting and the eccentric in a fixed axial location relative to the cutting head 94.

The system 10 also includes a hand tool 150 (shown in FIG. 1). The hand tool 150 holds the axial and rotary cables 20 and 18, respectively, adjacent the microkeratome 12 to facilitate holding and supporting the cables during an operation. Preferably the hand tool 150 holds the rotary drive cable 20 at an angle such that the end position of the rotary cable 20 will be substantially coaxial with the passage 140 in the cutting head 76 (see FIG. 7).

In operation, the rotary drive motor 60 produces a rotational motion in the rotary drive shaft 66 and the rotary drive shaft transmits the rotary motion to the fitting 145 and the eccentric 147. The eccentric and the vertical slot 138 in the blade holder 96 cooperate to transform the rotary motion of the eccentric to a transverse oscillating motion in the blade holder 96 and the cutting blade 98. The rotary drive shaft 66 preferably rotates at about twelve thousand five hundred revolutions per minute. Preferably the oscillating motion is perpendicular to the direction of motion of the cutting head 94 on the platform 76; however, the slots 114 and 138 in the cutting head and wedge; respectively, and/or the angle of the cutting edge 102 may be varied relative to the direction of motion of the cutting head to optimize the performance of the cutting blade 98.

The rotation created by the rotary drive motor 60 (FIG. 1) drives the oscillation of the cutting blade 98. The forward motion created by the axial drive motor 50 drives the cutting assembly 74 linearly or axially across the platform 72. The present invention permits independent adjustment of the speed and operation of the rotary drive motor and the axial drive motor. Thus different combinations of transverse cutting blade oscillation speed and axial speed across the cornea can be achieved. Furthermore, each motor may be operated alone, thereby producing, for example axial motion in the cutting blade without transverse oscillating motion, and vice versa.

As shown in FIG. 11, the suction tube 16 and the axial and rotary drive cables 20 and 18, respectively, connect to the microkeratome 12 from directions that minimize or eliminate the chance that a cable or tube would cross the circular opening 84 in the platform 76 where the cutting is performed. Preferably, the suction tube 16 and the axial and rotary cables 20 and 18, respectively, are aligned along the cutting direction with the cutting assembly 74 interposed between the suction tube on one side and the cables 18 and 20 on the other.

In summary, the disposable microkeratome 12 includes a cutting assembly 74 and platform assembly 72 combination. The platform assembly 72 is seated on the cornea of an eye and is fixedly located or held thereon. The microkeratome 12 is operated by a remotely located control assembly 14 that directs the movement of the cutting assembly 74 across the platform assembly 72 through two flexible cables 18 and 20.

As will be described in greater detail below with respect to a preferred embodiment, the controller 28 in the control assembly 14 controls the axial motor 50, the rotary motor 60, and the suction pump 26. Based on the description herein, it will be readily apparent to one skilled in the art to weigh the advantages and disadvantages of different control mechanisms and to select one suitable to carry out the present invention. The control assembly 14 can include any of numerous technologies available today or in the future, including but not limited to logic gate controllers, switches and relays, and software programming. Accordingly, one skilled in the art would appreciate that the scope of the present invention is intended to include all such suitable control mechanisms.

The operation of the ophthalmic surgical system 10 according to the present invention will be described below with reference to FIGS. 1 and 11–13. A sterile microkeratome 12 is connected to the control assembly 14 through the suction line 16 and the rotary and axial control cables 18 and 20, respectively, as described above.

Figure 13:
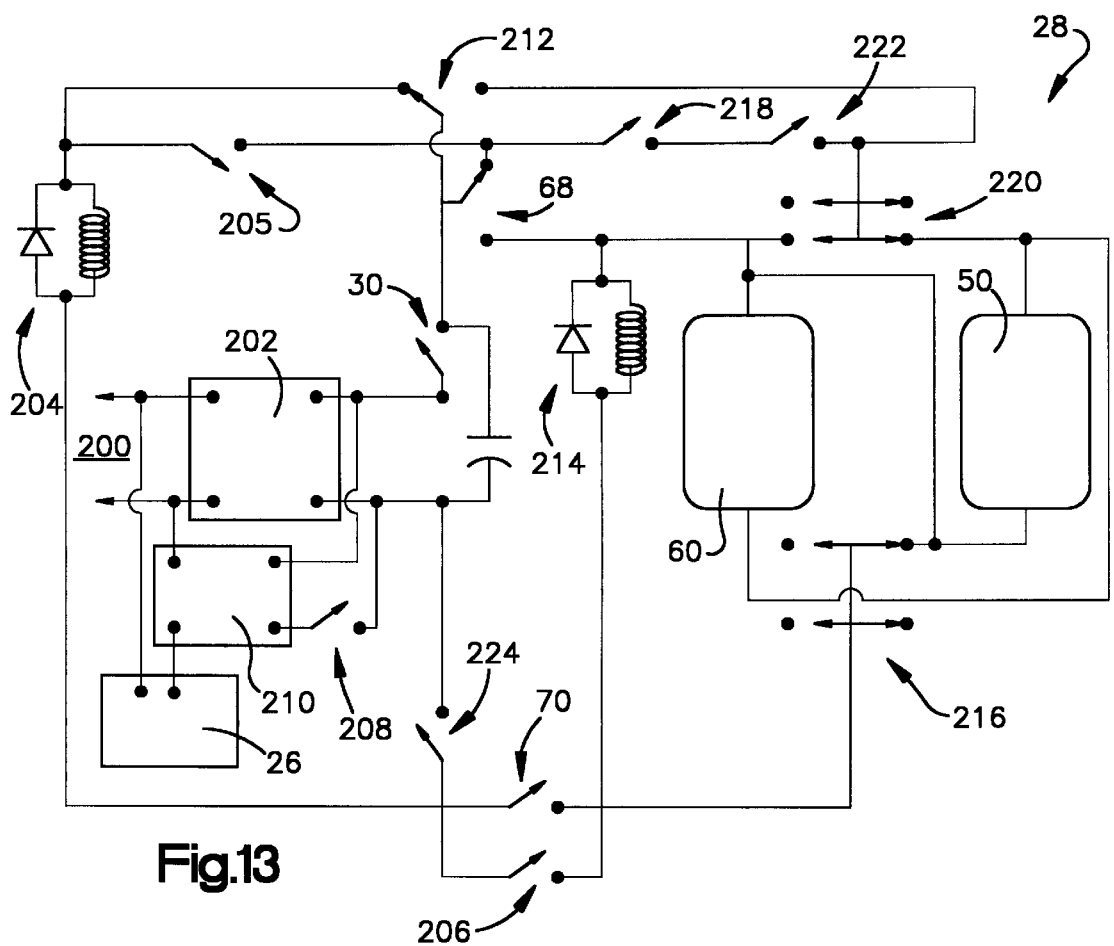
FIG. 13 is a schematic of the control system according to the present invention.

As shown in FIGS. 1 and 13, the system is powered up via an ON/OFF switch 30 or the like connected to a power source 200 through a transformer 202. Turning on the power energizes a first relay 204 and closes switches 205 and 206. The microkeratome 12 is placed over an eye to seat the suction chamber 86 on the eye with the cornea protruding through the opening 84 in the top surface 80 of the platform 76 (see FIG. 4). Suction is created in the suction line 16 by engaging the suction on/off switch 208 which activates the suction pump 26 through a solid state suction relay 210. The suction pump creates a partial vacuum in the suction chamber 86 (FIG. 4) to retain the platform 76 (FIG. 4) on the eye.

In other words, when the microkeratome 12 is placed over the eye such that the cornea protrudes from the suction chamber 86 through the opening 84 in the platform 76, the suction pump 26 secures the microkeratome in position on the eye. The microkeratome 12 advantageously can be completely connected to the control assembly 14 before it is placed on the eye. The connected microkeratome 12 is simply placed on the eye, suction is applied, and the surgeon can begin the operation.

Before the operation is started, however, the surgeon should select the desired flap length with the flap length adjustment selector 34 described above. The flap length adjustment selector 34 determines how far or how long to drive the axial motor 50 and thus drive the cutting assembly 74 across the opening 84 in the platform 76 to cut the cornea.

Once the surgeon is ready to begin, the two position foot pedal 32 is moved to a forward position and is held there, tripping switch 212. Preferably, the foot pedal 32 is biased to a neutral position between a reverse position and the forward position. When switch 212 is moved from its neutral position to its cut cycle initiate switch, the axial drive motor 50 is energized in a backward direction to retreat the slide member 52 and thus the cutting assembly carriage. The rotary drive motor 60 is not energized during this step and thus the cutting blade 98 (FIG. 4) does not oscillate. The slide member 52 continues to move in a reverse axial direction until the initial position microswitch 68 is tripped by the slide reaching a zero position.

Tripping the initial position microswitch 68 automatically stops the axial motor 50 and causes a second relay 214 to energize, the first relay 204 to de-energize, and to open switches 205 and 206. The first relay is linked to a direction switch 216 which moves from a reverse position to a forward position when the first relay is energized. The axial drive motor automatically begins to run in a forward axial direction. Simultaneously, the rotary motor 60 is energized to cause the cutting blade 98 (FIG. 4) to oscillate. The axial drive motor causes the cutting assembly carriage to move forward while the blade oscillates. Movement out of the slide's initial position will release the initial position microswitch 68 and allow it to return to its original state.

While continuing to hold the foot pedal 32 in its forward position, the slide member 52 advances, thereby advancing the cutting assembly carriage and transversely oscillating the cutting blade 98 until the hinge position microswitch 70 is tripped by the slide member 52 (or the controller 28 otherwise determines that the cut in the cornea that forms the flap is complete). Tripping the hinge position microswitch 70 stops both motors 50 and 60 automatically. If the foot pedal is released at any time during the cutting cycle, both motors will be stopped and the procedure must begin again from the start, with the cutting assembly returning to the initial position before advancing once again.

To complete the operation, the surgeon depresses the foot pedal 32 to the reverse position returning switch 212 to its original state and closing switch 218. The second relay 214 is de-energized and direction switches 216 and 220 move to reverse positions. The cutting assembly 74 moves in a reverse axial direction opposite the forward axial direction until the slide member 52 trips the initial position microswitch 68 and switch 222 opens and stops the motor 50. As a result of the combination of switches tripped in sequence, this does not lead to the automatic forward axial cutting motion that started the operation.

In order to secure an accurate operation and to avoid injury to the eye, the suction pump 26 should operate at all times to hold the microkeratome 12 on the eye while the flap is being cut. Accordingly, it is desirable for the controller 28 automatically to shut off the rotary and axial motors 60 and 50, respectively, whenever suction is lost or falls below a predetermined value, as determined for example by a pressure sensor switch 212. When the pressure sensor switch 224 opens due to loss of suction the axial and rotary drive motors 50 and 60 are shut off. The only available operation is to depress the foot pedal 32 to the reverse position. The axial motor 50 then runs in reverse to return the slide member 52 and the cutting head 94 to the initial position. As mentioned above, the rotary motor 60 does not operate when the axial motor 52 is running in reverse.

Accordingly, unlike prior art LASIK systems, the present invention provides a system which includes a control assembly which is remote from the microkeratome and which permits independent operation of the transverse and axial motions of the cutting blade. Furthermore, the microkeratome according to the present invention is advantageously substantially transparent, lightweight and disposable.

Although the invention has been shown and described with respect to a certain preferred embodiment or embodiments, equivalent alterations and modifications will occur to others skilled in the art upon the reading and understanding of this specification and the annexed drawings. In particular regard to the various functions performed by the above described integers (components, assemblies, devices, compositions, etc.), the terms (including a reference to a "means") used to describe such integers are intended to correspond, unless otherwise indicated, to any integer which performs the specified function of the described integer (i.e., that is functionally equivalent), even though not structurally equivalent to the disclosed structure which performs the function in the herein illustrated exemplary embodiment or embodiments of the invention. In addition, while a particular feature of the invention may have been described above with respect to only one of several illustrated embodiments, such feature may be combined with one or more other features of the other embodiments, as may be desired and advantageous for any given or particular application.

What is claimed is:

1. A microkeratome system for keratomileusis ophthalmic surgery comprising:

an axial cable having an axial shaft and a sheath, a base, a carriage mounted to the base and a cutting blade carried in the carriage, the carriage being guided by at least one guide on the base for movement in an axial cutting direction relative to the base and the cutting blade being movable in an oscillating direction transverse to the cutting direction, wherein the carriage is connectable to the axial cable, the axial shaft being movable within the sheath, and the base including an anchor configured for removable attachment of the sheath thereto to fix the sheath against movement relative to the base whereby axial movement of the shaft effects linear movement of the carriage relative to the base.

2. The microkeratome system of claim 1, wherein the anchor is an axial retaining clip mounted to the base.

3. The microkeratome system of claim 1, wherein the at least one guide retains the carriage adjacent the base and guides the movement of the carriage in the axial cutting direction.

4. The microkeratome system of claim 1, wherein the base has an opening extending from a top surface of the base to a suction chamber on a bottom side of the base, the suction chamber being adapted to be seated on an eye such that at least a portion of a cornea of the eye passes through the opening and protrudes above the top surface of the base.

5. The microkeratome system of claim 4, wherein the base includes a fixture having a passage therethrough to the suction chamber, the fixture being connectable to a vacuum source.

6. The microkeratome system of claim 1, wherein substantially all of the base and the carriage are molded from a substantially transparent material.

7. A microkeratome for keratomileusis ophthalmic surgery comprising:

a base, a carriage mounted to the base and a cutting blade carried in the carriage, the carriage being guided by at least one guide on the base for movement in an axial cutting direction relative to the base and the cutting blade being movable in an oscillating motion in an oscillating direction transverse to the cutting direction, wherein the carriage is connectable to an axial cable having an axial shaft such that axial movement of the shaft effects linear movement of the carriage relative to the base, and wherein the carriage includes a cutting head having an angled bottom surface with a transverse slot opening thereto, at least one recess in the angled bottom surface and a back surface with a passage extending therethrough to communicate with the transverse slot; a blade holder having a vertical slot and being received in the transverse slot of the cutting head for transverse movement therein, a portion of the blade holder extending below the bottom surface of the cutting head; the cutting blade having a cutting edge and a central opening, the blade holder engaging the central opening in the cutting blade for transverse movement therewith; a wedge having an angled top surface substantially parallel to the angled bottom surface of the cutting head with at least one protrusion extending therefrom to engage the at least one recess in the cutting head and hold the wedge against the cutting head and thereby retain the blade holder and cutting blade;

wherein the vertical slot in the blade holder communicates with the passage in the cutting head for receiving an eccentric on an end of a rotating shaft to convert rotational motion into a transverse oscillating motion of the blade holder and the cutting blade; and wherein the carriage is adapted to receive a connection to the axial shaft for moving the carriage across the base.

8. The microkeratome of claim 7, wherein the transverse slot is perpendicular to the angled bottom surface of the cutting head and the passage through the cutting head is parallel to the angled bottom surface.

9. The microkeratome of claim 7, wherein the carriage is adapted to receive a coupling adjacent the passage through the cutting head to retain the eccentric therein.

10. A system for keratomileusis ophthalmic surgery comprising:

a microkeratome for cutting a section of a cornea of an eye including a base, a carriage mounted to the base and a cutting blade carried in the carriage, the carriage being guided for linear movement in an axial direction relative to the base; and a control assembly for controlling the microkeratome, the control assembly including an axial drive for generating linear movement, the axial drive being connected to the microkeratome, wherein the axial drive includes an axial cable having an axial shaft and a sheath, the axial shaft connected to the carriage and movable within the sheath, and the base includes an anchor configured for removable attachment of the sheath thereto to fix the sheath against movement relative to the base such that axial movement of the axial shaft effects linear movement of the carriage relative to the base, a rotary drive for generating rotational movement independently of the axial drive, the rotary drive being connected to the microkeratome to impart an oscillating movement to the cutting blade transverse to the axial direction, and a controller which controls the axial drive and the rotary drive.

11. The system of claim 10, wherein the anchor is an axial retaining clip mounted to the base.

12. The system of claim 11, wherein the axial shaft is connected to the carriage with a coupling that permits the axial cable to rotate without imparting torque to the carriage.

13. The system of claim 10, wherein the control assembly includes a suction device for supplying suction pressure to the microkeratome, the suction device being connected to the microkeratome for generating a partial vacuum in a suction chamber mounted to the base to maintain a position of the base relative to an eye.

14. The system of claim 13, wherein the suction device includes a suction pump which is connected to the base of the microkeratome through a fixture having a passage therethrough to the suction chamber.

15. The system of claim 10, further comprising a plurality of microkeratomes which provide for respective different depths of cut, and the microkeratome connected to the control assembly is selected from the plurality of microkeratomes.

16. The system of claim 10, wherein the microkeratome is disposable and the control assembly is reusable.

17. The system of claim 10, wherein the control assembly further includes a slide member connected to the axial drive and the rotary drive, the slide member being movable through a range of linear motion by the axial drive;

wherein the rotary drive is mounted on the slide member for movement therewith;

wherein the slide member is connected to the microkeratome through the axial shaft; and wherein the rotary drive is connected to the microkeratome through a rotary shaft.

18. The system as set forth in claim 10, wherein the base and the carriage are formed of a molded transparent plastic material.

19. The system of claim 10, wherein the anchor is an axial retaining clip mounted to the base.

20. A system for keratomileusis ophthalmic surgery comprising:

a microkeratome for cutting a section of a cornea of an eye including
a base, a carriage mounted to the base and a cutting blade carried in the carriage, the carriage being guided for movement in an axial direction relative to the base; and a control assembly for controlling the microkeratome, the control assembly including
an axial drive for generating linear movement, the axial drive being connected to the microkeratome, wherein the axial drive includes an axial cable having an axial shaft connected to the carriage such that axial movement of the axial shaft effects linear movement of the carriage relative to the base, a rotary drive for generating rotational movement independently of the axial drive, the rotary drive being connected to the microkeratome to impart an oscillating movement in an oscillating direction to the cutting blade transverse to the axial direction, and a controller which controls the axial drive and the rotary drive, wherein the carriage includes a cutting head, a blade holder, and a wedge;

wherein the cutting head has an angled bottom surface with a transverse slot opening thereto, at least one recess therein and a back surface with a passage extending therethrough to the transverse slot;

wherein the blade holder has a vertical slot in a side thereof, the blade holder being received in the transverse slot for transverse movement therein with a portion of the blade holder extending below the bottom surface of the cutting head;

wherein the cutting blade has a cutting edge and a central opening, the blade holder engaging the central opening in the cutting blade for transverse movement therewith;

wherein the wedge has an angled top surface substantially parallel to the angled bottom surface of the cutting head with at least one protrusion extending therefrom to engage the at least one recess in the cutting head and hold the wedge against the cutting head and thereby retain the blade holder and blade;

wherein the rotary shaft has an eccentric on an end thereof which communicates with the vertical slot in the blade holder and cooperates therewith to convert the rotational motion of the rotary shaft into a transverse oscillating motion of the cutting blade; and wherein the axial shaft is connected to the carriage to impart axial movement thereto.

21. The system of claim 20, wherein the transverse slot is perpendicular to the angled bottom surface of the cutting head and the passage through the cutting head is parallel to the angled bottom surface.

22. The system of claim 20, wherein the carriage is adapted to receive a coupling adjacent the passage through the cutting head to retain the eccentric therein.

23. A method for keratomileusis ophthalmic surgery, comprising:

connecting an axial drive to a microkeratome to advance and retract a cutting blade along an axial direction; and linearly advancing the cutting blade of the microkeratome from an initial position in the axial direction while simultaneously oscillating the cutting blade in a direction transverse to the axial direction;

wherein connecting the axial drive to the microkeratome includes connecting an axial cable to the microkeratome, the microkeratome including a base and a carriage mounted on the base, the axial cable having an axial shaft and a sheath, the axial shaft being movable within the sheath, and the base including an anchor configured for removable attachment of the sheath thereto to fix the sheath against movement relative to the base whereby axial movement of the shaft effects linear movement of the carriage relative to the base; and connecting the axial cable to the microkeratome includes connecting the axial shaft to the carriage and connecting the sheath to the anchor.

24. The method of claim 23, further comprising:

connecting a rotary drive to the microkeratome to oscillate the cutting blade;

applying the microkeratome to an eye; and controlling the axial drive independently of the rotary drive.

25. The method of claim 23, further comprising selecting the microkeratome from a plurality of microkeratomes which provide for respective depths of cut.

26. The method of claim 23, further comprising disposing of a first microkeratome following a first operation and selecting a second microkeratome for a subsequent operation.

27. The method of claim 23, further comprising retaining the position of the microkeratome relative to an eye with a suction device that supplies suction pressure to the microkeratome to create a partial vacuum between the microkeratome and the eye.

28. A method for keratomileusis ophthalmic surgery, comprising:

connecting a disposable microkeratome to a control unit operative to drive and to control a cutting action of the microkeratome; and using the microkeratome to at least partially remove a section of a patient's cornea;

wherein connecting the disposable microkeratome to the control unit includes connecting an axial cable to the microkeratome, the microkeratome including a base and a carriage mounted on the base, the carriage carrying a cutting blade, the axial cable having an axial shaft and a sheath, the axial shaft being axially movable within the sheath, and the base including an anchor configured for removable attachment of the sheath thereto to fix the sheath against movement relative to the base whereby axial movement of the shaft effects linear movement of the carriage relative to the base; and connecting the axial cable to the microkeratome includes connecting the axial shaft to the carriage and connecting the sheath to the anchor.

29. A system for keratomileusis ophthalmic surgery comprising:

a microkeratome including a base, and a carriage mounted to the base for linear movement relative to the base; and a control assembly including at least one cable having a shaft and a sheath, the shaft being axially movable within the sheath, and the base includes an anchor configured for removable attachment of the sheath thereto to fix the sheath against movement relative to the base whereby axial movement of the shaft effects linear movement of the carriage relative to the base, the shaft is connected to the carriage and the sheath is connected to the anchor.

30. A system for keratomileusis ophthalmic surgery comprising: a microkeratome, a control assembly, and at least one flexible shaft connected between the microkeratome and the control assembly, the microkeratome including a base, and a carriage mounted to the base for movement in a first direction relative to the base, the carriage supporting a cutting blade for oscillating movement in a second direction transverse the first direction;

the control assembly having a frame, an axial drive mounted to the frame with a movable component movable relative to the frame for effecting axial movement of the at least one flexible shaft, and a rotary drive for effecting rotary movement of the at least one flexible shaft, the rotary drive mounted to the movable component of the axial drive for movement therewith;

whereby the axial movement of the at least one flexible shaft effects movement of the carriage and the rotary movement of the at least one flexible shaft effects oscillating movement of the cutting blade.

31. A system as set forth in claim 30, wherein the movable component includes a linearly movable slide member.

32. A system as set forth in claim 31, wherein the at least one flexible drive shaft includes a rotary shaft connected to the rotary drive and an axial shaft connected to the slide member such that linear movement of the slide member effects uniform linear movement of the axial shaft and the rotary shaft.

33. A system for keratomileusis opththalmic surgery comprising: a microkeratome including a base, and a carriage mounted to the base for movement in a first direction relative to the base, the carriage supporting a cutting blade for oscillating movement in a direction transverse the first direction; a control assembly including a first cable connected to the microkeratome for driving the movement of the carriage, a second cable connected to the microkeratome for driving the movement of the cutting blade in the second direction, and a holder adjacent the microkeratome and connected to the first cable and the second cable to maintain a substantially constant angle between the cables.

* * * * *